United States Patent
Nelson et al.

(10) Patent No.: US 10,038,975 B1
(45) Date of Patent: Jul. 31, 2018

(54) PROVISIONING NEWS ITEMS

(71) Applicant: Wells Fargo Bank, N.A., San Francisco, CA (US)

(72) Inventors: Corey Michael Nelson, Charlotte, NC (US); Spencer Holland Touchberry, Fort Mill, SC (US); November Michelle Champion, Richmond Heights, MO (US); Gwendoria M. Salley, Rock Hill, SC (US)

(73) Assignee: Wells Fargo Bank, N.A., San Francisco, CA (US)

( * ) Notice: Subject to any disclaimer, the term of this patent is extended or adjusted under 35 U.S.C. 154(b) by 0 days.

(21) Appl. No.: 15/348,574

(22) Filed: Nov. 10, 2016

(51) Int. Cl.
| | |
|---|---|
| *H04W 4/00* | (2018.01) |
| *H04W 4/02* | (2018.01) |
| *H04L 29/08* | (2006.01) |
| *H04B 1/3827* | (2015.01) |
| *G08B 5/38* | (2006.01) |
| *A61B 5/024* | (2006.01) |
| *G06Q 40/06* | (2012.01) |

(52) U.S. Cl.
CPC ......... *H04W 4/023* (2013.01); *A61B 5/02438* (2013.01); *G06Q 40/06* (2013.01); *G08B 5/38* (2013.01); *H04B 1/385* (2013.01); *H04L 67/22* (2013.01); *H04L 67/306* (2013.01); *H04B 2001/3861* (2013.01)

(58) Field of Classification Search
CPC .................................................. H04W 4/023
See application file for complete search history.

(56) References Cited

U.S. PATENT DOCUMENTS

| | | |
|---|---|---|
| 7,496,630 B2 | 2/2009 | Arellano et al. |
| 7,818,232 B1 | 10/2010 | Mead et al. |

(Continued)

FOREIGN PATENT DOCUMENTS

WO  WO-2015048181 A1   4/2015

OTHER PUBLICATIONS

Crouch, Michelle, "Push notifications: the future of bank communication", [Online]. [Accessed Jun. 10, 2016]. Retrieved from the Internet: <URL: http://www.bankingtech.com/205142/banking-on-you-how-wearable-tech-could-change-finance/>, (2016), 7 pgs.

(Continued)

*Primary Examiner* — Mazda Sabouri
(74) *Attorney, Agent, or Firm* — Schwegman Lundberg & Woessner, P.A.

(57) ABSTRACT

Various examples are directed to systems and methods for provisioning news items. A news provisioning application may apply user interest data to select a first news item from news data and determine that the first news item is negative for the first user based at least in part on the financial data. The news provisioning application may receive, from a first network-enabled device, physiological data describing a physiological condition of the first user at a first time and determine to provide the first news item to the first user based at least in part on the physiological data. The news provisioning application may send to a second network-enabled device, alert data instructing the second network-enabled device to modify the operation of the second network-enabled device to generate an alert indicating the first news item.

21 Claims, 11 Drawing Sheets

(56) References Cited

U.S. PATENT DOCUMENTS

| | | | |
|---|---|---|---|
| 8,458,077 | B2 | 6/2013 | Griffin et al. |
| 8,724,639 | B2 | 5/2014 | Mahmoud |
| 9,075,435 | B1 | 7/2015 | Noble et al. |
| 9,177,307 | B2 | 11/2015 | Ross et al. |
| 9,191,707 | B2 | 11/2015 | Jones et al. |
| 9,237,201 | B2 | 1/2016 | Papakipos et al. |
| 9,590,941 | B1* | 3/2017 | Itoh ................. H04L 51/24 |
| 2003/0088489 | A1 | 5/2003 | Peters et al. |
| 2012/0266076 | A1* | 10/2012 | Lockhart ......... G06F 17/30017 715/738 |
| 2014/0074935 | A1 | 3/2014 | Yadav-Ranjan |
| 2014/0243019 | A1* | 8/2014 | Jenkins ................. H04W 4/02 455/456.3 |
| 2015/0026060 | A1 | 1/2015 | Krietzman et al. |
| 2015/0193789 | A1* | 7/2015 | Gerard ............... G06Q 30/0202 705/7.31 |
| 2016/0066124 | A1 | 3/2016 | Chang et al. |
| 2016/0112357 | A1* | 4/2016 | Lineberger ............. H04L 51/12 709/204 |
| 2016/0112737 | A1* | 4/2016 | Johnston .......... H04N 21/44204 725/14 |
| 2016/0239737 | A1* | 8/2016 | Jiang ................... H04L 67/26 |
| 2016/0359791 | A1* | 12/2016 | Zhang .................. H04L 51/32 |
| 2017/0024767 | A1* | 1/2017 | Johnson, Jr. ....... G06Q 30/0261 |

OTHER PUBLICATIONS

Narain, Aman, "Banking on you—how wearable tech could change finance", Bankingtech, [Online]. [Accessed Jun. 10, 2016]. Retrieved from the Internet: <URL: http://www.bankingtech.com/205142/banking-on-you-how-wearable-tech-could-change-finance/>, (2016), 4 pgs.

* cited by examiner

PROVISIONING NEWS ITEMS

TECHNICAL FIELD

Embodiments described herein generally relate to systems and methods for utilizing one or more network-enabled devices in conjunction with environmental sensors and/or physiological sensors.

BACKGROUND

Investors receive financial and other news in many different ways. Many investors monitor network or cable television stations that provide general and financial news. Some investors utilize financial news web sites, applications, or other Internet sources. Some investors, such as professional investors, utilize proprietary news services, such as Bloomberg Professional® service available from Bloomberg L.P. of New York, N.Y.

DRAWINGS

In the drawings, which are not necessarily drawn to scale, like numerals may describe similar components in different views. Like numerals having different letter suffixes may represent different instances of similar components. Some embodiments are illustrated by way of example, and not of limitation, in the figures of the accompanying drawings, in which.

DETAILED DESCRIPTION

Figure 1:
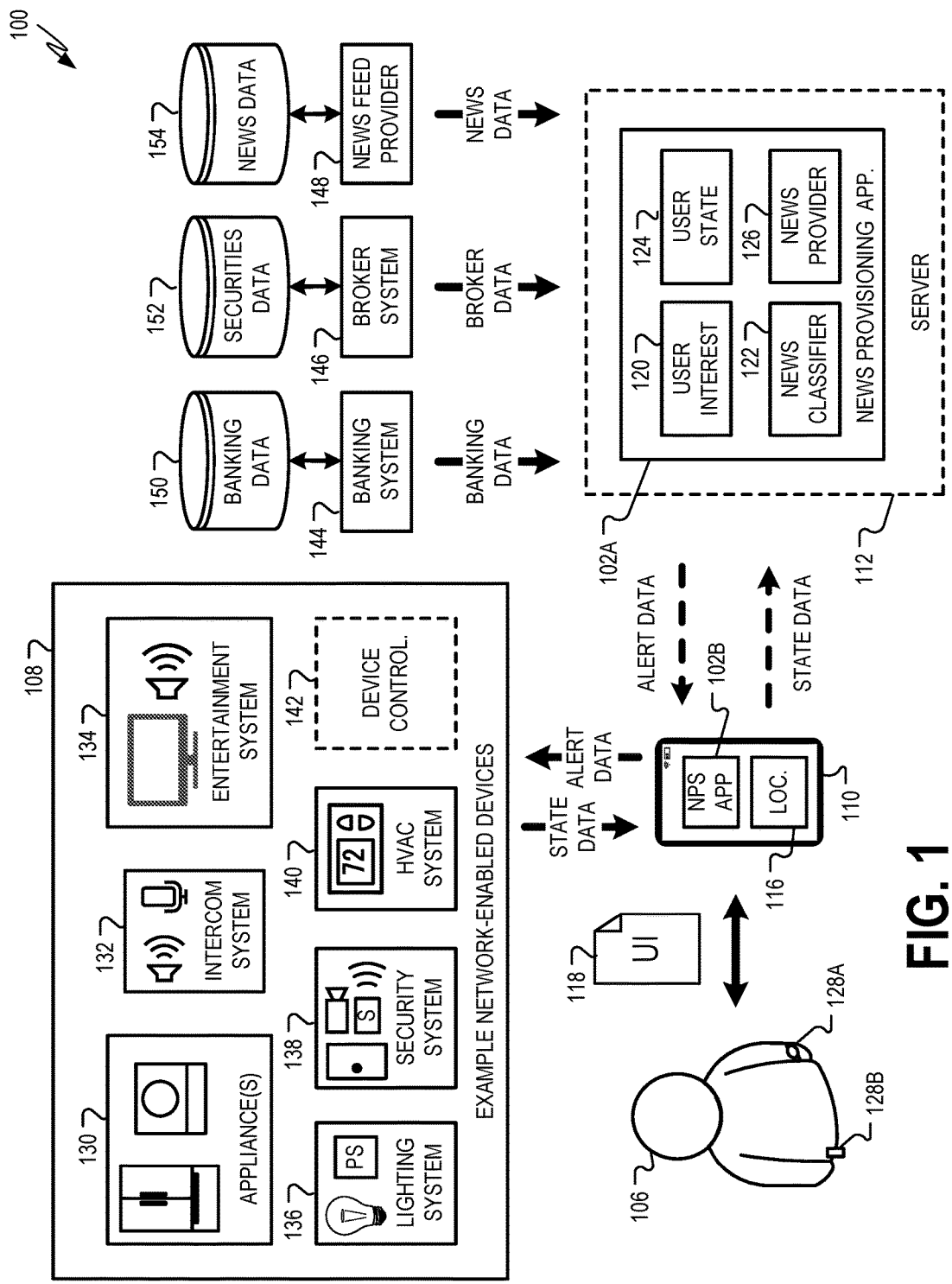
FIG. 1 is a diagram showing one example of an environment for provisioning news items to a user utilizing one or more network-enabled devices.

Investors or other users may monitor television, Internet, and/or proprietary financial news sources to receive and process news relevant to user's financial positions. Users, however, may not always have the time or inclination to follow the news constantly and make desirable adjustments to their financial holdings. For example, when a user is at home, the user may choose to engage in some activities that do not lend themselves to monitoring a telephone channel or Internet source. A state of the user may affect the user's willingness and/or capacity to react to some news items. For example, if the user is in the middle of a favorite television program, the user may only want to be disturbed for urgent news. Also, it may not be desirable for the user to receive negative news while the user is stressed, for example, to avoid health risks to the user, and/or because the user may not be prepared to react properly to negative news while stressed.

A news provisioning system, described herein, may be programmed to communicate with and utilize one or more network-enabled devices in the home or other location of an investor or other user to select news items for presenting to the user, select when a user's state permits the user to receive a news item, and select a medium for alerting the user of a news item. Network-enabled devices may include any device that includes hardware and/or software for communicating on a wired, wireless, or mixed data network.

The news provisioning system may receive a news feed including one or more news items. A news item may include a textual article, a video clip, etc., that conveys information about a current event, such as, for example, a current event affecting a financial holding or potential financial holding of the user. The news provisioning system may filter the news feed to select news items that are of interest to the user. The news provisioning system may also classify news items, for example, as positive or negative. The classifying may depend, for example, on an effect of the news item on actual or potential financial holdings of the user.

The news provisioning system may also determine a user state, for example, based on environmental and/or physiological factors. Environmental factors may include any factors describing the user's environment. For example, environmental factors may include the user's geographic location (e.g., home, work, or out), the user's position within the user's house (e.g., bedroom, living room, home gym, etc.), entertainment used by the user (e.g., television shows, podcasts, music, etc.), thermostat settings, state of the user's appliances, etc. Environmental data describing environmental factors may be received from any suitable devices. Physiological factors may include any factors that describe the user's physiological state. Examples include the user's heart rate, the user's breathing rate, the user's recent activity (steps walked, elevation climbed, etc.). The news provisioning system may determine environmental and physiological factors, for example, based on data received from network-enabled devices. For example, a wearable device may provide physiological factors. Environmental factors may be based on data received from various network-enabled devices such as the user's Global Positioning System (GPS)-enabled mobile computing device (e.g., user geographic location), a television or other entertainment system (e.g., entertainment consumed by the user), a security system (e.g., the user's current position in a house or building), a lighting system (e.g., the user's current location), etc. The news provisioning system may decide whether to provide a news item to the user based on the physiological data. For example, if the news is negative, and the physiological data indicates that the user is stressed, then the news provisioning system may delay providing the news item until the user's physiological state has changed.

In some examples, the news provisioning system may also select a medium for displaying a news item to a user. This may include sending an alert instruction to one or more network-enabled devices. For example, the news provisioning system may send an alert instruction to a network-enabled lighting system to blink or otherwise modify the state of lighting in the user's house or other building to alert the user that a news item is ready to be provided. The news provisioning system may provide the news item to a user computing device, an entertainment system, or other suitable device for creating a visual and/or audible representation of the news item for consumption by the user.

FIG. 1 is a diagram showing one example of an environment 100 for provisioning news items to a user utilizing one or more network-enabled devices. The environment 100 includes a primary news provisioning application 102A and a local news provisioning application 102B. The primary news provisioning application 102A may execute at a server 112. The server 112 may be implemented by a financial services provider, media/news provider, or any other suitable party providing the news provisioning system to a user 106. The local news provisioning application 102B may execute at a user computing device 110 of the user 106. The user computing device 110 may be or include, for example, a laptop computer, a desktop computer, a tablet computer, a smart phone, etc. In some examples, the user computing device 110 may also comprise a location subsystem 116 for determining a location of the user computing device 110. When the user 106 carries the user computing device 110, the location of the user computing device 110 also indicates the location of the user 106. The location subsystem 116 may include any suitable location hardware including, for example, Global Positioning System (GPS) hardware, etc.

The environment 100 also includes various example network-enabled devices 108. The example network-enabled devices 108 include one or more appliances 130, one or more intercom systems 132, one or more entertainment systems 134, one or more lighting systems 136, one or more security systems 138, one or more Heating Ventilation & Air Conditioning (HVAC) systems 140 and an optional device controller 142. Some of the example network-enabled devices 108 may include one or more sensors for sensing a state of the devices 108 and/or the surrounding environment.

Network-enabled devices 108 may include one or more network-enabled appliances 130. Network-enabled appliances 130 may include any suitable home appliance that is network-enabled. For example, network-enabled appliances may include a network-enabled refrigerator. The refrigerator may include one or more input devices, such as, a thermostat for measuring the temperature of the refrigerator, a thermostat for measuring the temperature of a freezer included with the refrigerator, a door latch sensor for the refrigerator and/or freezer to measure instances where the respective doors open, a camera to capture an image of goods in the refrigerator, etc. The refrigerator may also include one or more output devices such as, for example, a light inside the refrigerator or associated freezer, a display on an exterior or interior panel of the refrigerator, one or more exterior lights, a speaker, etc.

Another example of a network enabled appliance 130 is a washer for clothes. The washer may include input devices such as a counter for counting the number of cycles executed by the washer, a door latch sensor for sensing when the machine is open or closed, a temperature gauge for measuring the temperature of water used in the washer, a detergent presence sensor for sensing the presence of and/or amount of detergent used in the washer, etc. The washer may include output devices such as, for example, a display, one or more exterior lights, a speaker, etc. Other examples of network-enabled appliances 130 may include microwave ovens, toasters, stand-alone freezers, hot water heaters, mixers, coffee makers, etc.

Network-enabled devices 108 may also include one or more network-enabled intercom systems 132. An network-enabled intercom system 132 may include one or more microphones (e.g., input devices) as well as one or more speakers (output devices) positioned around a house or other structure associated with the user 106. The network-enabled intercom system 132, in some examples, also includes one or more cameras for capturing images and/or displays for showing images.

Network-enabled devices 108 may also include one or more network-enabled entertainment systems 134. Network-enabled entertainment systems 134 may include one or more televisions or other displays, speakers, audio/video receivers, video disk players, etc. In some examples, a television, speakers and other components may be aggregated into a single network-enabled entertainment system 134. In some examples, an individual television, audio receiver, etc., may act as a network-enabled entertainment system 134.

Network-enabled devices 108 may also include one or more lighting systems 136. A network-enabled lighting system 136 may include one or more lights and, in some examples, one or more photosensors or other sensors for sensing a light level. For example, photosensors may be input devices while lights may be output devices. In some examples, a network-enabled lighting system 136 may include various other input/output devices such as light switches, light control devices, etc.

Network-enabled devices 108 may also include one or more network-enabled security systems 138. A network-enabled security system 138 may include sensors for sensing conditions at the home or other location where the network-enabled security system 138 is located. For example, one or more cameras may capture images at various positions at the home or other location. One or more motion and/or proximity sensors may sense motion and/or presence at various positions at the home or other locations. In some examples, one or more door sensors may sense the state of one or more doors to the home or other location. Door states may include "open" and "closed," for example. The network-enabled security system 138 may also comprise a keypad or other control device or application for managing the state of the system 138. The keypad, as well as sensors, such as cameras, proximity detectors, motion detectors, door state detectors, etc., may be input devices to the network-enabled security system 138. Some network-enabled security systems 138 may also have output devices such as, for example, a display, a siren or other audible alarm generator, various lights, etc.

Network-enabled devices 108 may also include one or more network-enabled HVAC systems 140. A network-enabled HVAC system 140 may include one or more HVAC devices, such as a furnace, air conditioner, etc. A network-enabled HVAC system 140 may also include one or more thermostats or other devices or applications for controlling the operation of the HVAC device or devices.

An optional device controller 142 may comprise one or more computing devices programmed to act as an interface between the news provisioning application 102A, 102B and the various other network-enabled devices 108. For example, the news provisioning application 102A, 102B may communicate with the device controller 142 in lieu of communicating directly with the individual network-enabled devices 108.

The environment 100 may also include network-enabled devices, such as wearables 128A, 128B, that sense physiological data describing the user 106. Wearables 128A, 128B may be or include any suitable type of wearable device such as, for example, a watch, a device to clipped to a belt or other location of the user 106, etc. Wearables 128A, 128B may include one or more sensors such as, for example, accelerometers, gyroscopic sensors, etc., that sense movement of the user 106. These sensors may be input devices configured to sense steps, altitude changes, etc., of the user 106, which may indicate the user's level of physical activity. Wearables 128A, 128B may also include microphones, pressure sensors, electrodes, etc., for measuring the user's heart rate, breathing rate, blood pressure, and/or other physiological conditions.

The primary news provisioning application 102A may comprise various subsystems, 120, 122, 124, 126 for processing news items for the user 106. For example, a user interest subsystem 120 may determine interests for the user 106, for example, from data received from network-enabled devices 108, 110, 128A, 128B, etc. A news classifier subsystem 122 may classify received news items, for example, as being of interest to the user 106 and/or of being positive or negative relative to the user 106. A user state subsystem 124 may determine a state of the user, for example, from physiological data received from the network-enabled wearables 128A, 128B or other similar devices. A news provider subsystem 126 may select news items to provide to the user 106, select a provision medium for providing the news items to the user 106, and provide alert data (including news items) to the local news provisioning application 102B.

In the example shown, the primary news provisioning application 102A is in communication with various data provider systems including, for example, a banking system 144 comprising a banking system data store 150, a broker system 146 comprising a securities data store 152, and a news feed provider 148 comprising a news data store 154. Although one example of each system 144, 146, 148 is shown, some implementations of the environment 100 will include multiple examples of one or more of the systems 144, 146, 148.

The local news provisioning application 102B may receive state data from the various network-enabled devices 108, 128A, 128B, 110. State data may include data captured by input devices of the respective devices 108, 128A, 128B, 110. (For example, the user computing device 110 may capture its location utilizing the location subsystem 116, which may indicate the location of the user 106). The local news provisioning application 102B, for example, may be in communication with the user computing device 110, the wearables 128A, 128B and some or all of the example network-enabled devices 108 (either directly or through one or more device controllers 142). The local news provisioning application 102B may also receive alert data from the primary news provisioning application 102A and provide the alert data to the appropriate network-enabled devices 108, 128A, 128B, 110, which may provide the alert data to the user 106.

In some examples, the local news provisioning application 102B may also generate a graphical user interface 118 for provision to the user 106. For example, the user 106 may configure the applications 102A, 102B and/or receive news items and alerts via the user interface 118.

The example of the environment 100 shown in FIG. 1 shows just one way that the tasks of news provisioning can be divided between the primary news provision application 102A and the local news provisioning application 102B. Any other suitable arrangement may be used. Also, in some examples, the local news provisioning application 102B may be omitted. For example, the primary news provisioning application 102A may communicate directly with the network-enabled devices 108, 128A, 128B, 110, and may provide the UI 118 to the user 106 (e.g., via the user computing device 110). Additionally, in some examples, primary news provisioning application 102A may be omitted and/or executed at the user computing device 110. For example, the local news provisioning application 102B may be in communication with the banking system 144, the broker system 146, and/or the news feed provider 148 and/or may comprise subsystems, such as subsystems 120, 122, 124, 126.

Figure 2:
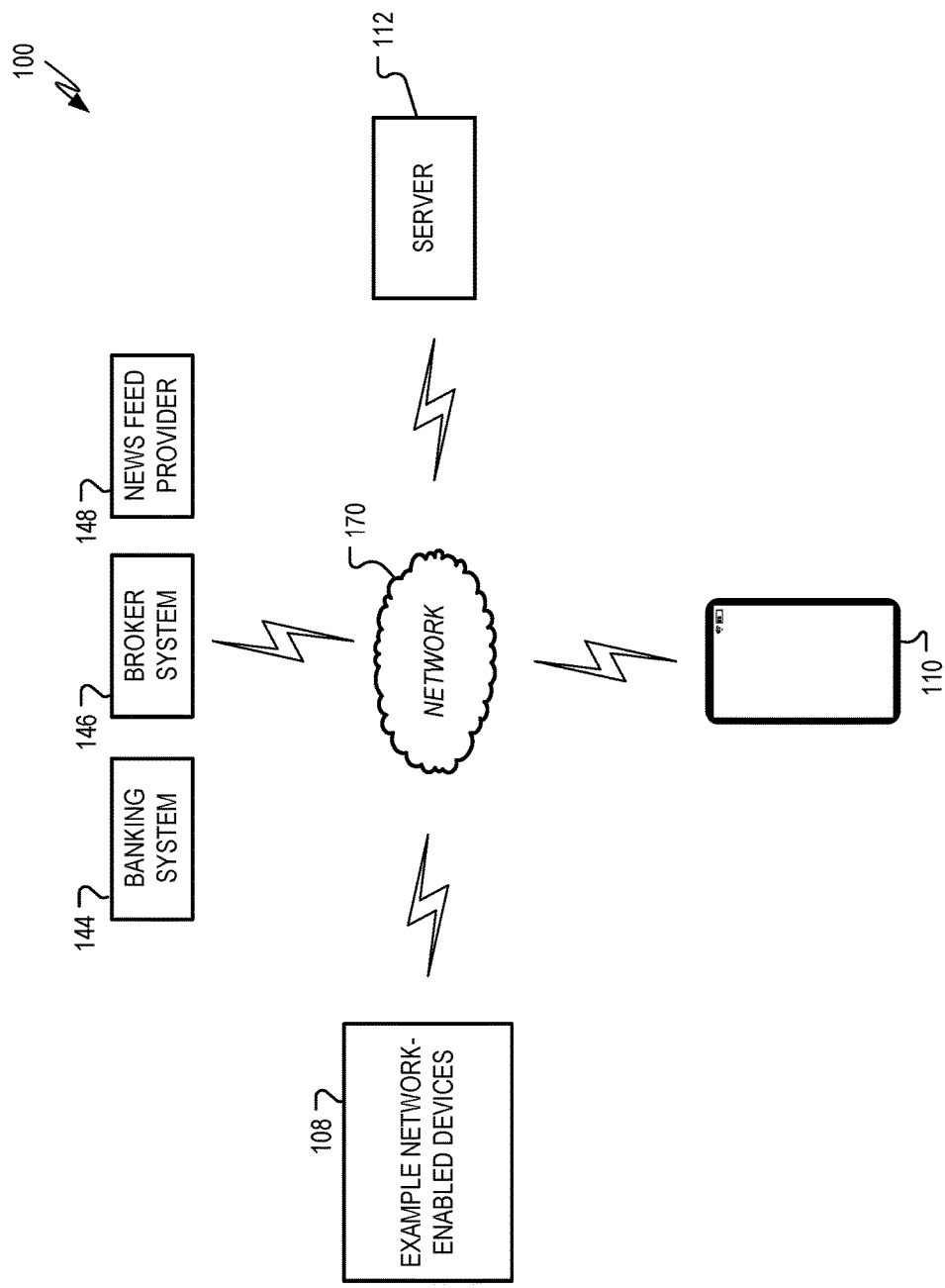
FIG. 2 is a diagram showing another example of the environment including a network.

FIG. 2 is a diagram showing another example of the environment 100 including a network 170. The various components 144, 146, 148, 108, 110, 112 of the environment 100 may be in communication with one another via a network 170. The network 170 may be or comprise any suitable network element operated according to any suitable network protocol. For example, one or more portions of the network 170 may be an ad hoc network, an intranet, an extranet, a virtual private network (VPN), a local area network (LAN), a wireless LAN (WLAN), a wide area network (WAN), a wireless WAN (WWAN), a metropolitan area network (MAN), a portion of the Internet, a portion of the Public Switched Telephone Network (PSTN), a cellular telephone network, a wireless network, a Wi-Fi network, a WiMax network, another type of network, or a combination of two or more such networks.

Figure 3:
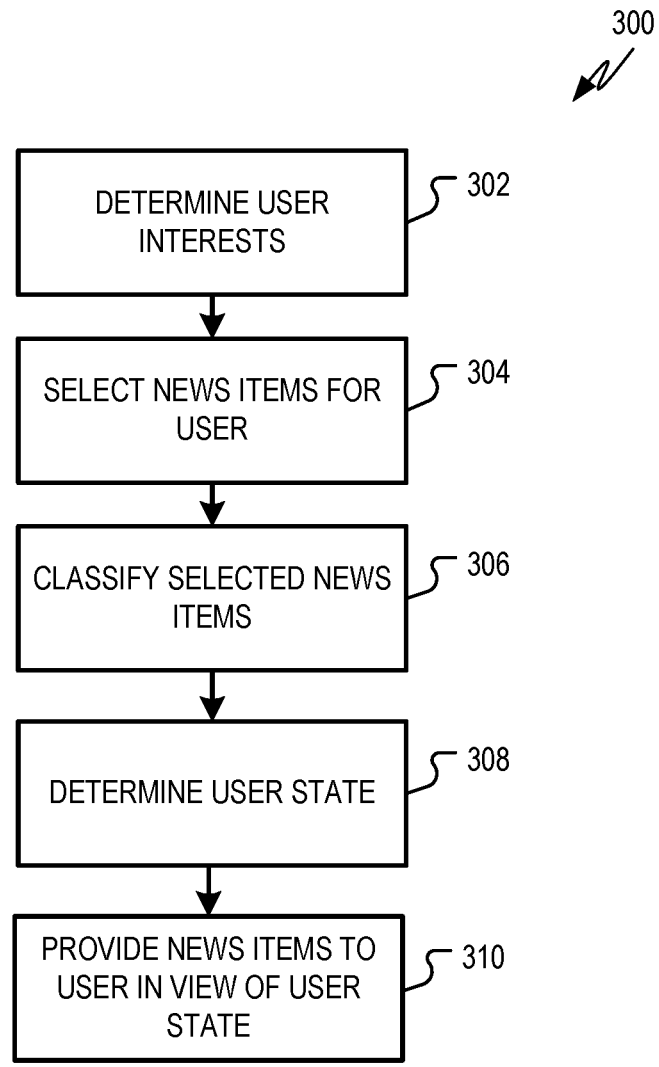
FIG. 3 is a flow chart showing one example of a process flow that may be executed in the environment of FIG. 1 to provide news items to the user.

FIG. 3 is a flow chart showing one example of a process flow 300 that may be executed in the environment 100 to provide news items to the user 106. In the description of FIG. 3, the operations of the process flow 300 are described as being executed by the news provisioning application. Operations described as being executed by the news provisioning application and/or by various subsystems 120, 122, 124, 126 described in FIG. 1 may be executed by any combination of the primary news provisioning application 102A and the local news provisioning application 102B.

At operation 302, the news provisioning application (e.g., the user interest subsystem 120) may determine user interests for the user 106. User interests may be determined based on any combination of inputs from network-enabled devices 108, 128A, 128B, 110. For example, FIG. 4 includes additional examples describing a determination of user interests. At operation 304, the news provisioning application (e.g., the news classifier subsystem 122) may select news items for the user, for example, from a news feed from a news feed provider 148. The selected news items may be consistent with the interests of the user 106 determined at operation 302. At operation 306, the news provisioning application (e.g., the news classifier subsystem 122) may classify the selected news items as positive or negative, for example, in view of the holdings and/or potential holdings of the user 106. Additional examples describing the selection and classification of news items are provided herein with respect to FIG. 5.

At operation 308, the news provisioning application (e.g., the user state subsystem 124) may determine a state of the user, for example, based on physiological data describing a physiological condition of the user and/or other data such as the user's location, etc. Additional examples describing the determination of user state are described herein with respect to FIG. 6. At operation 310, the news provisioning application (e.g., the news provider subsystem 126) may provide one or more news items to the user 106, for example, in view of the user state determined at operation 308. For example, if a news item is negative for the user 106, the news provisioning application may not provide the news item unless the user state indicates that the user 106 is prepared to receive negative news.

The news provisioning application may provide the news item by sending alert data to one or more network-enabled device. The alert data may instruct the network-enabled device to modify its ordinary operation to provide an alert that indicates the news item. For example, if the network-enabled device is a lighting system, it may modify its ordinary operation by changing its current mode of operation (e.g., turning on a light that was off, turning off a light that was on, blinking a light, etc.). Additional details of providing a news item to the user 106 are provided herein with respect to FIGS. 7-8.

Figure 4:
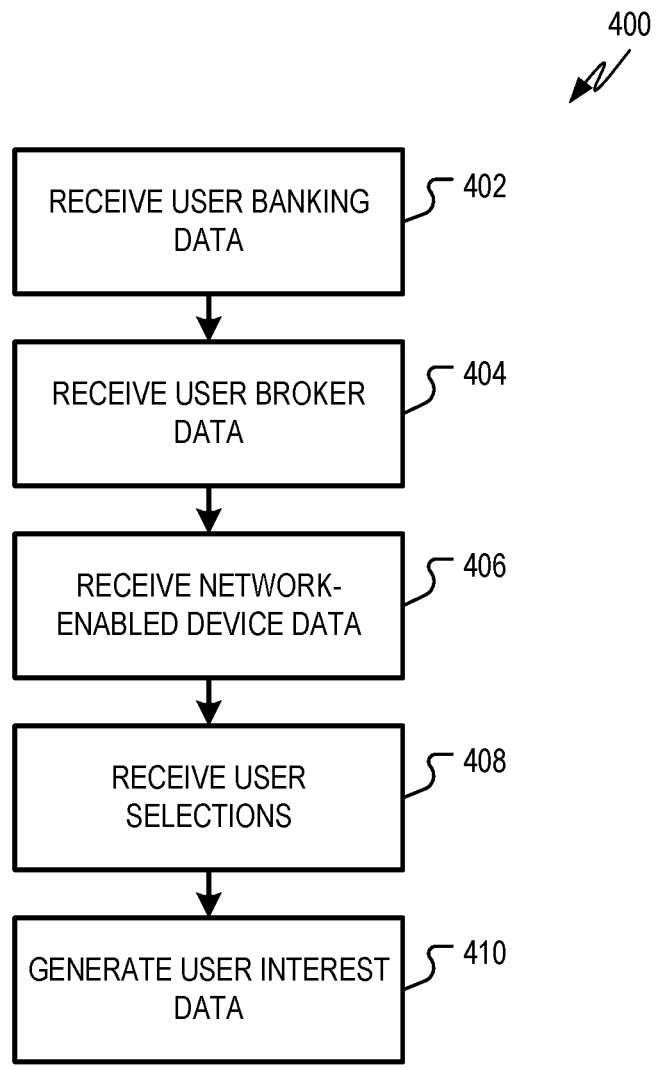
FIG. 4 is a flow chart showing one example of a process flow that may be executed in the environment of FIG. 1 to determine user interests of the user.

FIG. 4 is a flow chart showing one example of a process flow 400 that may be executed in the environment 100 to determine user interests of the user 106. In the description of FIG. 4, the operations of the process flow 400 are described as being executed by the user interest subsystem 120. As described above, the user interest subsystem 120 may be a component of the primary news provisioning application 102A and/or of the remote news provisioning application 102B.

At operation 402, the user interest subsystem 120 may receive user banking data, for example, from one or more banking systems 144. User banking data may describe bank accounts held by the user 106. Bank accounts may include bank accounts typically handled by a retail bank, such as checking accounts, savings accounts, certificates of deposit, etc. At operation 404, the user interest subsystem 120 may receive user broker data, for example, from one or more broker systems 146. The user broker data may describe one or more securities positions held by the user 106. Securities positions may include stock positions, mutual fund positions, options or other derivatives held by the user 106, etc. Banking data and/or broker data may be or include user financial data.

At operation 406, the user interest subsystem 120 may receive additional user data from one or more network-enabled devices 108, 128A, 128B, 110. The type of data received may depend on the type of device from which it is received. The user computing device 110 may provide location data describing where the user 106 spends his or her time. For example, a user 106 who spends time at baseball games may be interested in news items relating to baseball. A user 106 who spends time at an industry trade show may be interested in news items relating to that industry. Wearables 128A, 128B may provide physiological data describing the user 106. For example, a user 106 with high blood pressure may be interested in news items relating to pharmaceutical companies that make high blood pressure medication.

Example network-enabled devices 108 may provide additional data describing the user 106. For example, one or more network-enabled appliances may provide appliance usage data. In some examples, a refrigerator may provide usage data describing the foods consumed by the user 106 and/or his or her household. A network-enabled washer or dryer may provide usage describing a number of cycles or loads of clothes washed, a frequency of loads, a size of loads, etc. A network-enabled security system 138 may provide data describing where the user 106 spends time in his or her house and/or when the user 106 comes and goes from his or her house. For example, a user 106 spending a large amount of time in the kitchen may be interested in cooking and/or companies that make cooking utensils and appliances. A network-enabled HVAC system 140 may provide data describing the user's temperature preferences. For example, a user 106 who keeps their thermostat set to warm temperatures in the winter may be interested in news items relating to energy companies.

At operation 408, the user interest subsystem 120 may, optionally, receive user interest selections. For example, the user 106 may provide data describing one or more news item categories or other descriptors that are of interest to the user. In some examples, the user 106 may provide user interest selection data through the user interface 118.

At operation 410, the user interest subsystem 120 may generate user interest data for the user. The user interest data may describe news items that are of interest to the user, for example, in view of the data received at operations 402, 404, 406, 408. In some examples, the user interest data may be based on actual or potential financial holdings of the user 106. For example, actual financial holdings may be determined from banking data and broker data received from the banking system 144 and broker system 146. Potential financial holdings may be determined in view of user activities or properties received from network-enabled devices 108, 128A, 128B, 110. For example, the user interest subsystem 120 may apply rules that apply user behaviors, objects present in the user's house, and/or other factors to identify potential financial holdings of the user.

For example, a user 106 who frequents movie theaters may have a potential financial holding in stock for movie theater chains. The user interest subsystem 120 may receive banking data from the banking system 144 indicating that the user has purchased more than a threshold number of movie tickets. As a result, the user interest subsystem 120 may generate interest data identifying movie theater chains as potential financial holdings of the user.

Also, for example, the user interest subsystem 120 may monitor user behavior based on network-enabled appliances 130, the HVAC system 140, the security system 138, etc. to identify user behaviors that indicate potential financial holdings. In one example rule, the user interest subsystem 120 may identify potential financial holding in an energy company or energy companies for a user 106 who keeps their thermostat set higher than average.

In another example, the user interest subsystem 120 may utilize a network-enabled appliance (e.g., refrigerator), a security system 138 or other network-enabled device to identify purchased or other products in the user's house and tie those products to potential financial holdings. For example, the user interest subsystem 120 may apply one or more rules concluding that a user who buys a particular product is a potential investor in companies that manufacture the product and/or constituent components. For example, a user 106 within appliance usage data indicating that the user 106 keeps a particular brand of catsup in their refrigerator may have a potential financial holding in the maker of the catsup and/or competitors. A user 106 with appliance usage data indicating that the user 106 keeps a particular brand of mayonnaise in the refrigerator may have a potential financial holding in the maker of the mayonnaise. For example, a network-enabled refrigerator may comprise a camera positioned to capture an image of the mayonnaise and extract from the image an indication of the brand or other indication of origin.

User interest data describing user interests may take any suitable form. In some examples, user interest data includes a set of rules to be applied against news items in a news feed. For example, news items tagged with one or a combinations of subject matter tags indicated by the user interest data may be considered of interest to the user 106.

Figure 5:
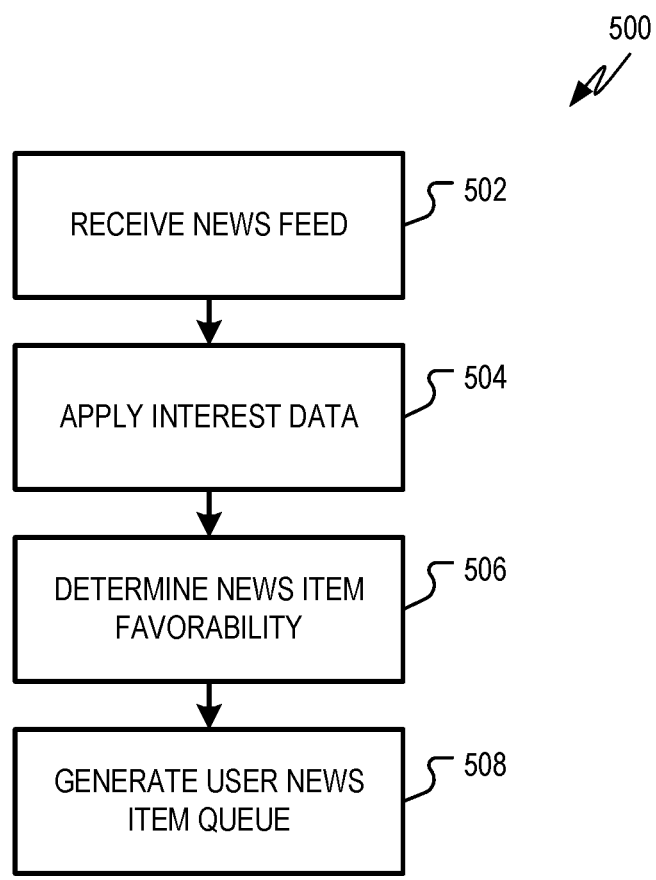
FIG. 5 is a flow chart showing one example of a process flow that may be executed in the environment of FIG. 1 to select news items for the user.

FIG. 5 is a flow chart showing one example of a process flow 500 that may be executed in the environment 100 to select news items for the user 106. In the description of FIG. 5, the operations of the process flow 500 are described as being executed by the news classifier subsystem 122. As described above, the news classifier subsystem 122 may be a component of the primary news provisioning application 102A and/or of the remote news provisioning application 102B.

At operation 502, the news classifier subsystem 122 may receive a news feed, for example, from one or more news feed providers 148. The news feed may include a plurality of news items. A news item may include a textual article, video clip, etc. that conveys information about a current event, such as, for example, a current event affecting a financial holding or potential financial holding of the user. In some examples, the news feed is continuously updated by the news feed provider 148. For example, the news feed provider 148 may provide news items as the news items are generated.

At operation 504, the news classifier subsystem 122 may apply the interest data generated by the user interest subsystem 120 to select one or more news items from the news feed that are of interest to the user 106. At operation 506, the news classifier subsystem 122 may determine the favorability of the selected news items to the user 106. A news item may be considered favorable if it indicates an increase in the value of a financial holding or a potential financial holding of the user 106. A news item maybe consider unfavorable if it indicates a decrease in the value of a financial holding or a potential financial holding of the user 106.

At operation 508, the news classifier subsystem 122 may generate a user news data structure, such as a queue or stack, comprising the selected news item. The data structure may have a next news item position for the next news item to be removed from the stack. In a First In First Out (FIFO) data structure, such as a queue, the next news item position may indicate the news item that was "first in" to the data structure. In a Last In First Out (LIFO) data structure, such as a stack, the next news item position may indicate the news item that was "last in" to the data structure.

Figure 6:
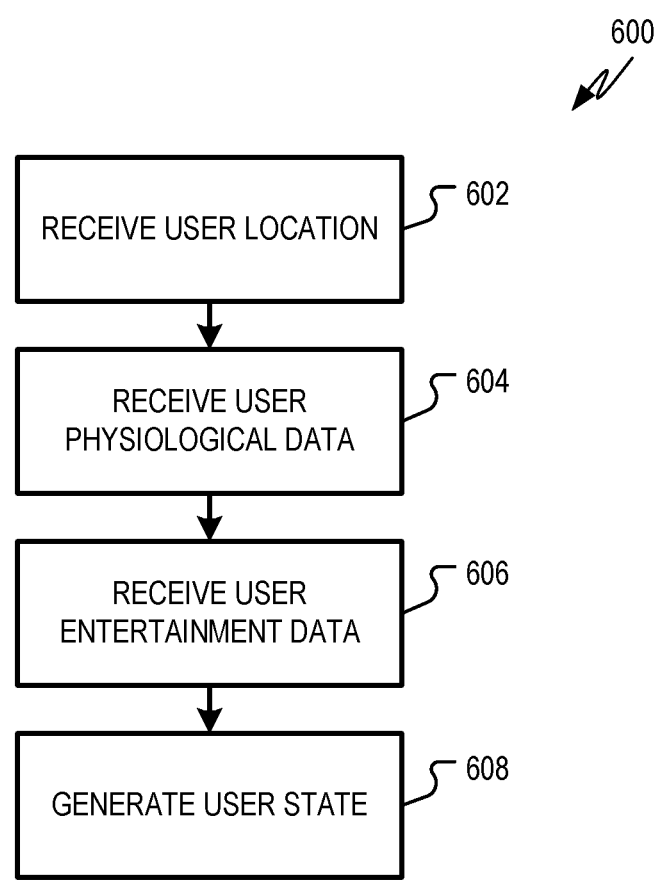
FIG. 6 is a flow chart showing one example of a process flow that may be executed in the environment of FIG. 1 to determine a user state of the user.

FIG. 6 is a flow chart showing one example of a process flow 600 that may be executed in the environment 100 to determine a user state of the user 106. In the description of FIG. 6, the operations of the process flow 600 are described as being executed by the user state subsystem 124. As described above, the user state subsystem 124 may be a component of the primary news provisioning application 102A and/or of the remote news provisioning application 102B.

At operation 602, the user state subsystem 124 may receive location data describing a location of the user 106. For example, the location data may originate from the user computing device 110, and/or another network-enabled device associated with the user 106 (e.g., one or more of wearables 128A, 128B may also include GPS or other location hardware or software). At operation 604, the user state subsystem 124 may receive user physiological data. User physiological data may indicate a physiological condition of the user 106. User physiological data may be received from, for example, a wearable network-enabled device, such as wearables 128A, 128B, or anther network-enabled device that includes a sensor or sensors positioned to sense physiological data regarding a user. Physiological data may include, for example, heart rate data describing the user's heart rate, blood pressure data describing the user's blood pressure, breathing rate data indicating the user's breathing rate, activity data indicating a recent activity of the user (e.g., steps taken, distance walked, elevation changes, calories burned, active minutes in a given period, etc.).

At operation 606, the user state subsystem 124 may receive user entertainment data, for example, from the network-enabled entertainment system 134, the user computing device 110 or other network-enabled device that can provide entertainment content to the user 106. The user entertainment data may indicate entertainment content being consumed by the user 106. For example, user entertainment data may include data describing a television show being watched by the user 106, a podcast being listed to by the user 106, etc.

At operation 608, the user state subsystem 124 may generate user state data. Generating user state data may include aggregating and/or summarizing the data received at operations 602, 604, 606, 608. In some examples, user state data may also include a characterization of the data received at operations 602, 604, 606, 608. For example, if the user 106 is watching a favorite television show, the user state data may indicate that the user 106 is to be disturbed for urgent news items only. Also, for example, if the user's blood pressure, breathing rate, etc., is about a threshold value, then user data may indicate that the user 106 is stressed and that it would not be ideal to provide negative news items to the user 106.

Figure 7:
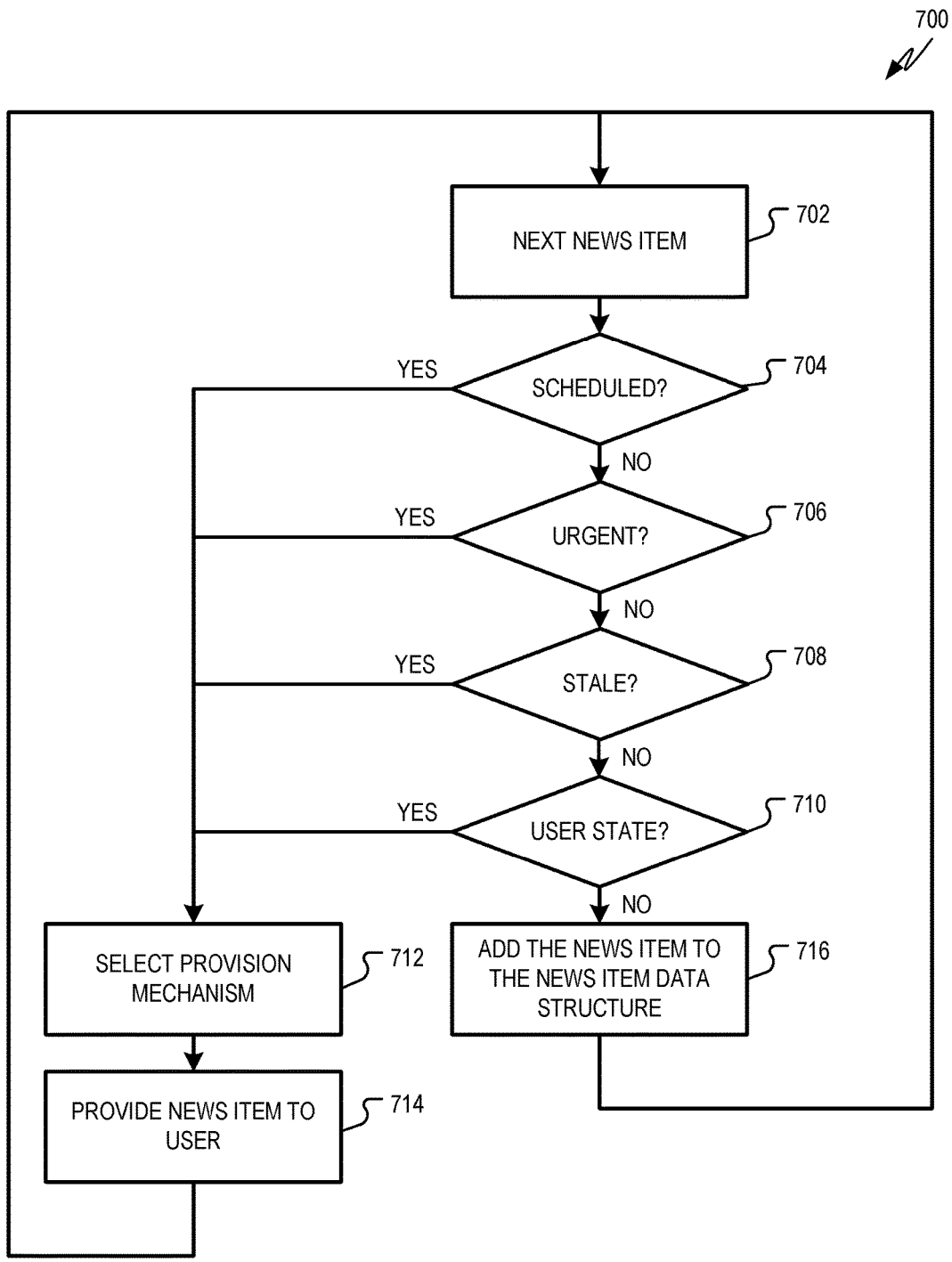
FIG. 7 is a flow chart showing one example of a process flow that may be executed in the environment to provide news items to the user, for example, from a news item data structure.

FIG. 7 is a flow chart showing one example of a process flow 700 that may be executed in the environment 100 to provide news items to the user 106, for example, from a news item data structure. In the description of FIG. 7, the operations of the process flow 700 are described as being executed by the news provider subsystem 126. As described above, the news provider subsystem 126 may be a component of the primary news provisioning application 102A and/or of the remote news provisioning application 102B.

At operation 702, the news provider subsystem 126 may take up a next news item. For example, the next news item may be the news item at the next news item position of the news item data structure generated as described with respect to the process flow 500. At operation 704, the news provider subsystem 126 may determine if the news item is scheduled to be provided to the user 106 at the current time. For example, the user 106 or other party may configure the news provisioning application to provide certain news items a predetermined time. For example, the user 106 may wish to receive one or more news items related to a particular stock exchange upon closing of that exchange. If the news item is scheduled to be delivered, the news provider sub system 126 may proceed to provide the news item to the user 106, for example, as described at operations 712 and 714. If not, the news provider subsystem 126 may proceed to operation 706.

At operation 706, the news provider subsystem 126 may, optionally, determine whether the news item is urgent. A news item may be considered urgent, for example, if the potential impact of the news item on actual and/or potential financial holdings of the user 106 is greater than a threshold value. Also, in some examples, a news item may be considered urgent based on any other suitable criteria. If the news item is urgent, the news provider sub system 126 may proceed to provide the news item to the user 106, for example, as described at operations 712 and 714. If not, the news provider subsystem 126 may proceed to operation 708.

At operation 708, the news provider subsystem 126 may, optionally, determine if the news item is stale. A news item may be stale, for example, if it has been cycled through the news item data structure more than a threshold number of times and/or for more than a threshold time. For example, the news item may be negative and the user's stress level may have been too high to receive the news item at the previous times when the news item came up for consideration at the next news item position of the news item data structure. If the news item is stale, the news provider sub system 126 may proceed to provide the news item to the user 106, for example, as described at operations 712 and 714. If not, the news provider subsystem 126 may proceed to operation 710.

At operation 710, the news provider subsystem 126 may determine if the user state permits provision of the news item. This may be determined, for example, based on the news item and/or the user state. For example, if the user is exercising, or watching a favorite television program, the user state may not permit provision of the news item. If the user state indicates that the user is stressed and the news item is negative, then the user state may not permit provision of the news item. If the user state permits provision of the news item, the news provider sub system 126 may proceed to provide the news item to the user 106, for example, as described at operations 712 and 714. If not, the news provider subsystem 126 may add the news item back to news item data structure at operation 716 and proceed again to operation 702 to consider the news item that is at the next news item position of the news item data structure after the previously-considered news item is re-added. For example, if the news item data structure is a LIFO data structure, the next news item may be the same news item that was just considered.

Referring now to operation 712, the news provider subsystem 126 may select a provision mechanism for the news item. For example, the provision mechanism may include an output of one or more network-enabled devices. In some examples, the provision mechanism may be selected based on the type of the news item. For example, an urgent news item and/or a highly negative or highly positive news item may be indicated by prominent outputs of network-enabled devices. In some examples, the provision mechanism may be selected based on a user preference received via the user interface 118.

At operation 714, the news provider subsystem 126 may provide the news item to the user 106. For example, the news provider subsystem 126 may generate alert data and send the alert data to one or more network-enabled devices of the environment 100. As described herein, the alert data may instruct the network-enabled devices to deviate from normal operation in one or more ways. In some examples, upon providing a news item, the news provisioning application may prompt the user 106 to make one or more financial transactions in response to the news. For example, if the news item relates to a security, the user may be prompted to take a long or short position in the security (e.g., depending on whether the news was positive or negative). In some examples, if the user 106 decides to make a financial transaction, the news provisioning application may prompt the user 106 to enter a communications session with the broker system 146 to execute the financial transaction.

In some examples, the news provisioning application may be configured to provide private news items to the user 106. Private news items, for example, may describe the user's actual or potential financial holdings. In some examples, the user 106 may provide rules or factors that may be used to determine if a news item or other data is private.

Figure 8:
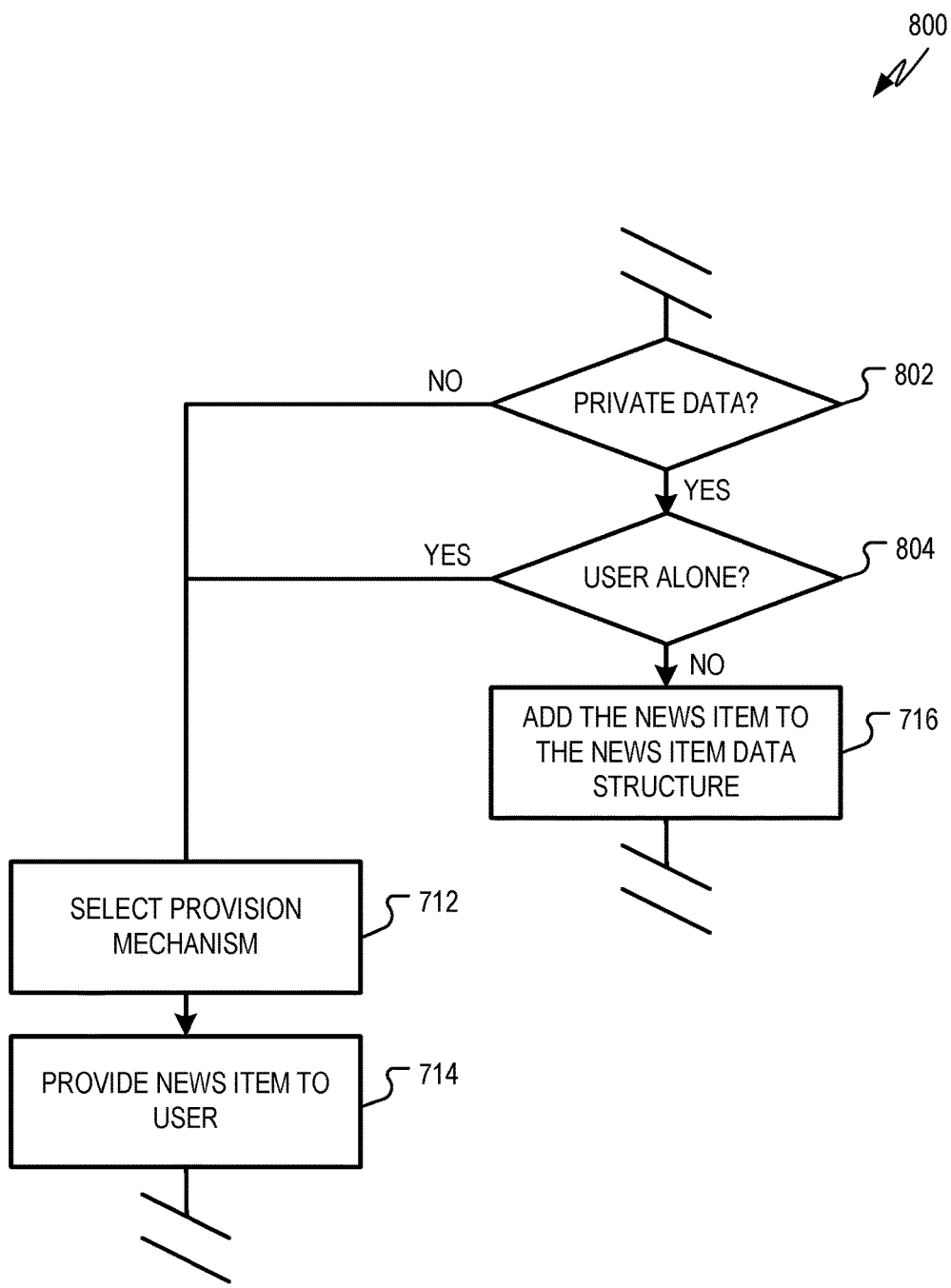
FIG. 8 is a flow chart showing one example of a process flow for providing news items to the user showing additional conditions that may be considered for providing news items to the user.

FIG. 8 is a flow chart showing one example of a process flow 800 for providing news items to the user showing additional conditions that may be considered for providing news items to the user 106. For example, operations 802 and 804 may be incorporated into the process flow 700, for example, before, after, or between the operations 704, 706, 708, or 710. In the description of FIG. 8, the operations of the process flow 800 are described as being executed by the news provider subsystem 126. As described above, the news provider subsystem 126 may be a component of the primary news provisioning application 102A and/or of the remote news provisioning application 102B.

At operation 802, the news provider subsystem 126 may determine if a considered news item is private. A news item may be private, for example, if it relates to a topic, financial holding, and/or potential financial holding that the user 106 has indicated is private, for example, via the user interface 118. If not, the news provider subsystem 126 may proceed to provide the news item to the user 106 at operations 712 and/or 714, as described. If the news item is private, the news provider subsystem 126 may determine, at operation 804, whether the user is alone. For example, the news provider subsystem 126 may query one or more network-enabled devices to determine whether the user is alone. In some examples where the user 106 is at home (e.g., as indicated by user computing device 110), the news provider subsystem 126 may determine if the user 106 is alone by querying the network-enabled security system 138. For example, a motion detector, camera, etc., of the network-enabled security system 138 may indicate whether the user 106 is alone. If the user 106 is alone, the news provider subsystem 126 may provide the news item to the user 106, as described. If the user 106 is not alone, the news provider subsystem 126 may proceed to operation 716 as described.

Figure 9:
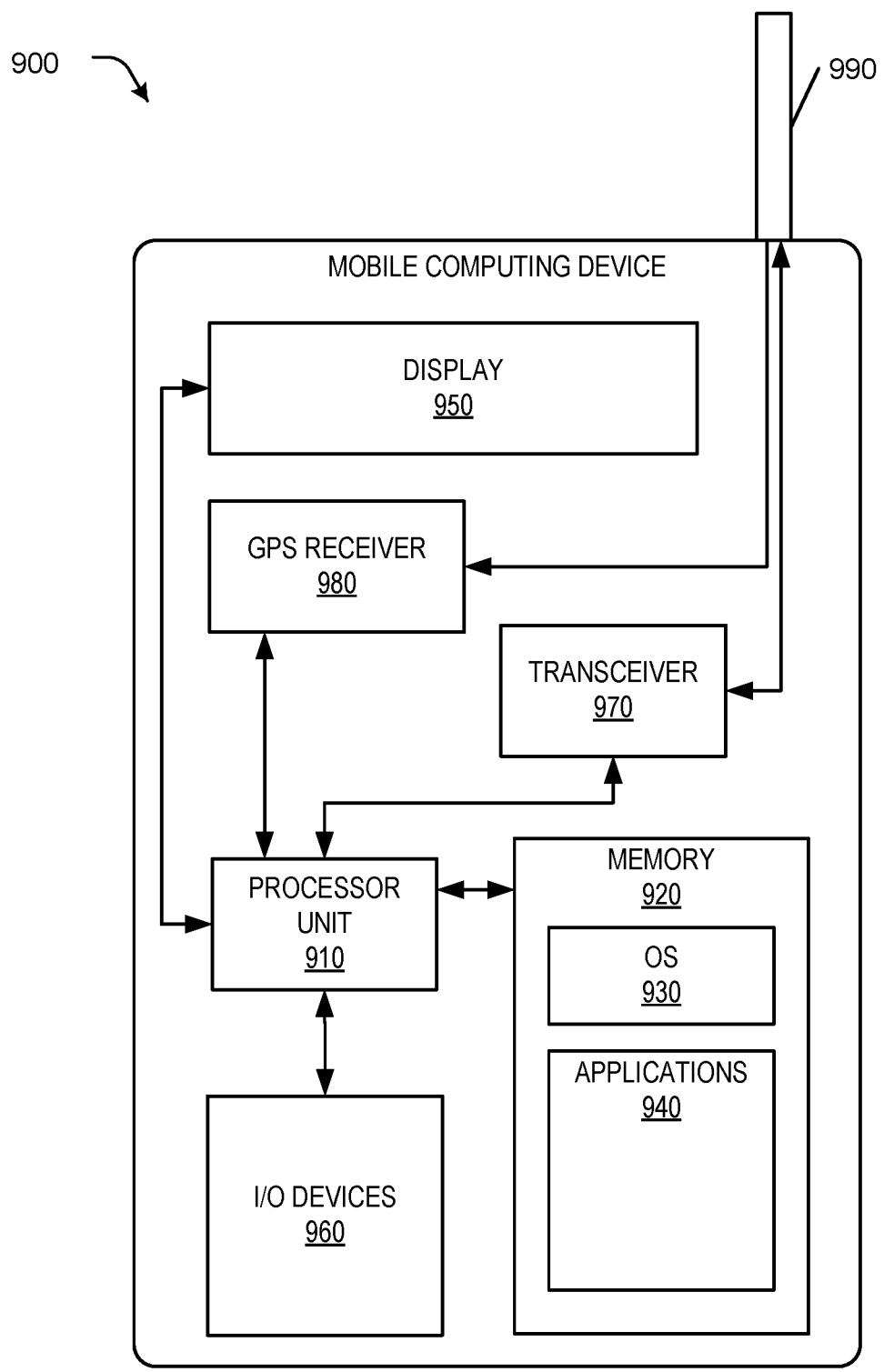
FIG. 9 is a block diagram showing one example of a software architecture for a computing device.

FIG. 9 is a block diagram showing an example architecture 900 of a mobile computing device. For example, the architecture 900 may describe any of the network-enabled devices 108, 128A, 128B, 110, etc., described herein. The architecture 900 comprises a processor unit 910. The processor unit 910 may include one or more processors. Any of a variety of different types of commercially available processors suitable for mobile computing devices may be used (for example, an XScale architecture microprocessor, a Microprocessor without Interlocked Pipeline Stages (MIPS) architecture processor, or another type of processor). A memory 920, such as a Random Access Memory (RAM), a Flash memory, or other type of memory or data storage, is typically accessible to the processor unit 910. The memory 920 may be adapted to store an operating system (OS) 930, as well as application programs 940. In some examples, the OS 930 may implement software interrupts that cause the architecture 900 to pause its current task and execute an interrupt service routine (ISR) when an interrupt is received.

The processor unit 910 may be coupled, either directly or via appropriate intermediary hardware, to a display 950 and to one or more input/output (I/O) devices 960, such as a keypad, a touch panel sensor, a microphone, and the like. Such I/O devices 960 may include a touch sensor for capturing fingerprint data, a camera for capturing one or more images of the user, a retinal scanner, or any other suitable devices. Similarly, in some examples, the processor unit 910 may be coupled to a transceiver 970 that interfaces with an antenna 990. The transceiver 970 may be configured to both transmit and receive cellular network signals, wireless data signals, or other types of signals via the antenna 990, depending on the nature of the mobile computing device implemented by the architecture 900. Although one transceiver 970 is shown, in some examples, the architecture 900 includes additional transceivers. For example, a wireless transceiver may be utilized to communicate according to an IEEE 902.11 specification, such as Wi-Fi and/or to a short range communication medium. Some short range communication mediums, such as NFC, may utilize a separate, dedicated transceiver. Further, in some configurations, a GPS receiver 980 may also make use of the antenna 990 to receive GPS signals. In addition to or instead of the GPS receiver 980, any suitable location-determining sensor may be included and/or used, including, for example, a Wi-Fi positioning system. In some examples, the architecture 900 (e.g., processor unit 910) may also support a hardware interrupt. In response to a hardware interrupt, the processor unit 910 may pause its processing and execute an interrupt service routine (ISR). For example, alert data may include and/or trigger a hardware interrupt. The ISR for the hardware interrupt may cause the network-enabled device to deviate from its normal operation, as described herein.

Figure 10:
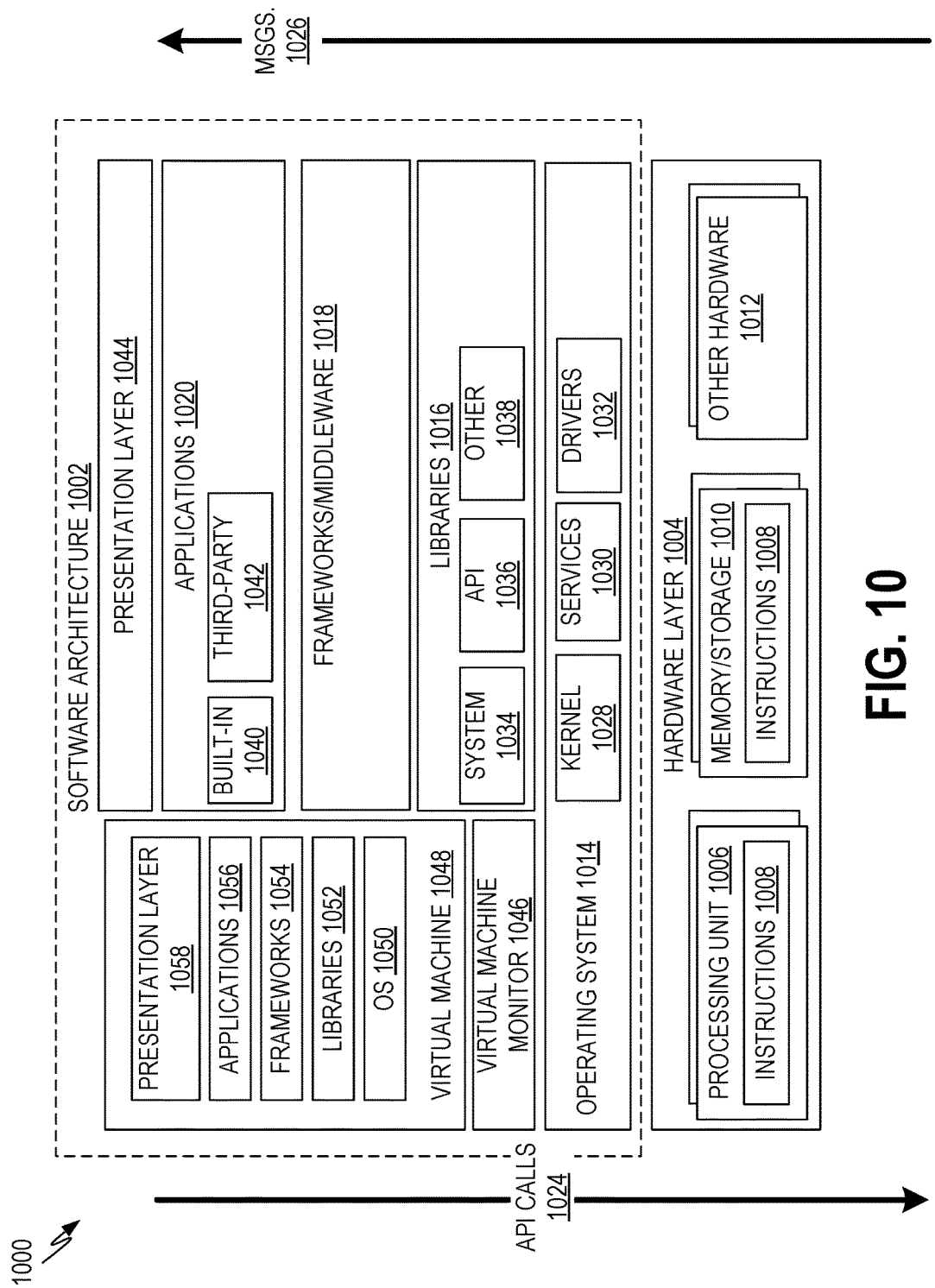
FIG. 10 is a block diagram illustrating a computing device hardware architecture, within which a set or sequence of instructions can be executed to cause the machine to perform examples of any one of the methodologies discussed herein.

FIG. 10 is a block diagram 1000 showing one example of a software architecture 1002 for a computing device. The architecture 1002 maybe used in conjunction with various hardware architectures, for example, as described herein. FIG. 10 is merely a non-limiting example of a software architecture 1002 and many other architectures may be implemented to facilitate the functionality described herein. The software architecture 1002 may be executed on hardware such as, for example, any of the network-enabled devices 108, 128A, 128B, 110, etc., described herein. A representative hardware layer 1004 is illustrated and can represent, for example, any of the above referenced computing devices. In some examples, the hardware layer 1004 may be implemented according to the architecture 1002 of FIG. 10 and/or the architecture 1100 of FIG. 11.

The representative hardware layer 1004 comprises one or more processing units 1006 having associated executable instructions 1008. Executable instructions 1008 represent the executable instructions of the software architecture 1002, including implementation of the methods, modules, components, and so forth of FIGS. 1-8. Hardware layer 1004 also includes memory and/or storage modules 1010, which also have executable instructions 1008. Hardware layer 1004 may also comprise other hardware as indicated by other hardware 1012, which represents any other hardware of the hardware layer 1004, such as the other hardware illustrated as part of hardware architecture 1100.

In the example architecture of FIG. 10, the software architecture 1002 may be conceptualized as a stack of layers where each layer provides particular functionality. For example, the software architecture 1002 may include layers such as an operating system 1014, libraries 1016, frameworks/middleware 1018, applications 1020 and presentation layer 1044. Operationally, the applications 1020 and/or other components within the layers may invoke application programming interface (API) calls 1024 through the software stack and receive a response, returned values, and so forth illustrated as messages 1026 in response to the API calls 1024. The layers illustrated are representative in nature and not all software architectures have all layers. For example, some mobile or special purpose operating systems may not provide a frameworks/middleware layer 1018, while others may provide such a layer. Other software architectures may include additional or different layers.

The operating system 1014 may manage hardware resources and provide common services. The operating system 1014 may include, for example, a kernel 1028, services 1030, and drivers 1032. The kernel 1028 may act as an abstraction layer between the hardware and the other software layers. For example, the kernel 1028 may be responsible for memory management, processor management (e.g., scheduling), component management, networking, security settings, and so on. The services 1030 may provide other common services for the other software layers. In some examples, the services 1030 include an interrupt service. The interrupt service may detect the receipt of an interrupt and, in response, cause the architecture 1002 to pause its current processing and execute an interrupt service routine (ISR) when an interrupt is received.

The drivers 1032 may be responsible for controlling or interfacing with the underlying hardware. For instance, the drivers 1032 may include display drivers, camera drivers, Bluetooth® drivers, flash memory drivers, serial communication drivers (e.g., Universal Serial Bus (USB) drivers), Wi-Fi® drivers, NFC drivers, audio drivers, power management drivers, and so forth depending on the hardware configuration.

The libraries 1016 may provide a common infrastructure that may be utilized by the applications 1020 and/or other components and/or layers. The libraries 1016 typically provide functionality that allows other software modules to perform tasks in an easier fashion than to interface directly with the underlying operating system 1014 functionality (e.g., kernel 1028, services 1030 and/or drivers 1032). The libraries 1016 may include system libraries 1034 (e.g., C standard library) that may provide functions such as memory allocation functions, string manipulation functions, mathematic functions, and the like. In addition, the libraries 1016 may include API libraries 1036 such as media libraries (e.g., libraries to support presentation and manipulation of various media format such as MPEG4, H.264, MP3, AAC, AMR, JPG, PNG), graphics libraries (e.g., an OpenGL framework that may be used to render 2D and 9D in a graphic content on a display), database libraries (e.g., SQLite that may provide various relational database functions), web libraries (e.g., WebKit that may provide web browsing functionality), and the like. The libraries 1016 may also include a wide variety of other libraries 1038 to provide many other APIs to the applications 1020 and other software components/modules.

The frameworks 1018 (also sometimes referred to as middleware) may provide a higher-level common infrastructure that may be utilized by the applications 1020 and/or other software components/modules. For example, the frameworks 1018 may provide various graphic user interface (GUI) functions, high-level resource management, high-level location services, and so forth. The frameworks 1018 may provide a broad spectrum of other APIs that may be utilized by the applications 1020 and/or other software components/modules, some of which may be specific to a particular operating system or platform.

The applications 1020 includes built-in applications 1040 and/or third-party applications 1042. Examples of representative built-in applications 1040 may include, but are not limited to, a contacts application, a browser application, a book reader application, a location application, a media application, a messaging application, and/or a game application. Third party applications 1042 may include any of the built-in applications 1040 as well as a broad assortment of other applications. In a specific example, the third-party applications 1042 (e.g., an application developed using the Android™ or iOS™ software development kit (SDK) by an entity other than the vendor of the particular platform) may be mobile software running on a mobile operating system such as iOS™, Android™, Windows® Phone, or other mobile computing device operating systems. In this example, the third-party applications 1042 may invoke the API calls 1024 provided by the mobile operating system such as operating system 1014 to facilitate functionality described herein.

The applications 1020 may utilize built-in operating system functions (e.g., kernel 1028, services 1030 and/or drivers 1032), libraries (e.g., system libraries 1034, API libraries 1036, and other libraries 1038), frameworks/middleware 1018 to create user interfaces to interact with users of the system. Alternatively, or additionally, in some systems, interactions with a user may occur through a presentation layer, such as presentation layer 1044. In these systems, the application/module "logic" can be separated from the aspects of the application/module that interact with a user.

Some software architectures utilize virtual machines. In the example of FIG. 10, this is illustrated by virtual machine 1048. A virtual machine creates a software environment where applications/modules can execute as if they were executing on a hardware computing device. A virtual machine is hosted by a host operating system (operating system 1014) and typically, although not always, has a virtual machine monitor 1046, which manages the operation of the virtual machine 1048 as well as the interface with the host operating system (i.e., operating system 1014). A software architecture executes within the virtual machine 1048 such as an operating system 1050, libraries 1052, frameworks/middleware 1054, applications 1056 and/or presentation layer 1058. These layers of software architecture executing within the virtual machine 1048 can be the same as corresponding layers previously described or may be different.

Figure 11:
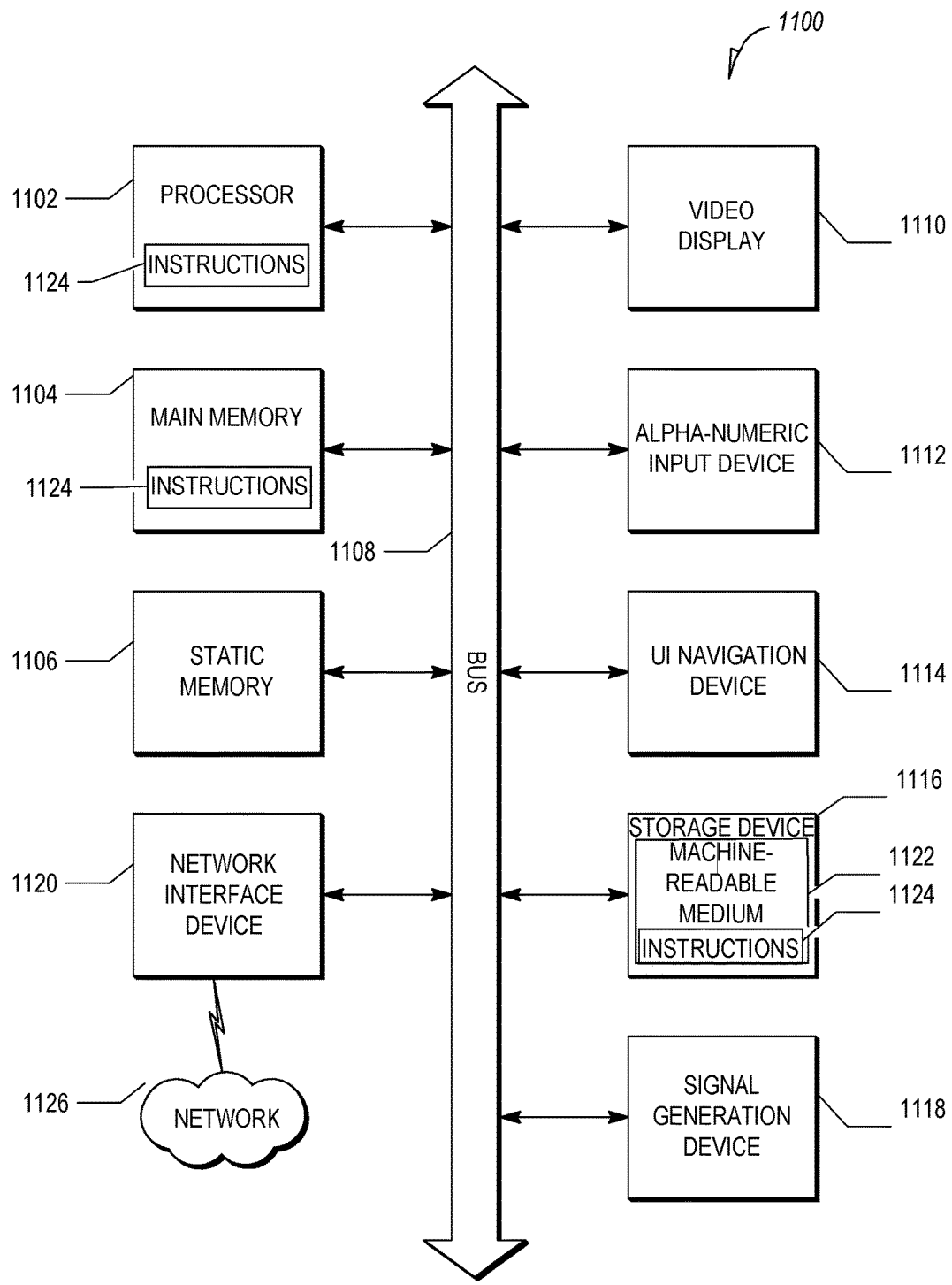
FIG. 11 is a block diagram illustrating a computing device hardware architecture within which a set or sequence of instructions can be executed to cause the machine to perform examples of any one of the methodologies discussed herein.

FIG. 11 is a block diagram illustrating a computing device hardware architecture 1100, within which a set or sequence of instructions can be executed to cause the machine to perform examples of any one of the methodologies discussed herein. For example, the architecture 1100 may execute the software architecture 1002 described with respect to FIG. 10. The architecture 1100 may operate as a standalone device or may be connected (e.g., networked) to other machines. In a networked deployment, the architecture 1100 may operate in the capacity of either a server or a client machine in server-client network environments, or it may act as a peer machine in peer-to-peer (or distributed) network environments. The architecture 1100 can be implemented in a personal computer (PC), a tablet PC, a hybrid tablet, a set-top box (STB), a personal digital assistant (PDA), a mobile telephone, a web appliance, a network router, switch or bridge, or any machine capable of executing instructions (sequential or otherwise) that specify actions to be taken by that machine.

Example architecture 1100 includes a processor unit 1102 comprising at least one processor (e.g., a central processing unit (CPU), a graphics processing unit (GPU) or both, processor cores, compute nodes, etc.). The architecture 1100 may further comprise a main memory 1104 and a static memory 1106, which communicate with each other via a link 1108 (e.g., bus). The architecture 1100 can further include a video display unit 1110, an alphanumeric input device 1112 (e.g., a keyboard), and a user interface (UI) navigation device 1114 (e.g., a mouse). In some examples, the video display unit 1110, input device 1112 and UI navigation device 1114 are incorporated into a touch screen display. The architecture 1100 may additionally include a storage device 1116 (e.g., a drive unit), a signal generation device 1118 (e.g., a speaker), a network interface device 1120, and one or more sensors (not shown), such as a global positioning system (GPS) sensor, compass, accelerometer, or other sensor.

In some examples, the processor unit 1102 or other suitable hardware component may support a hardware interrupt. In response to a hardware interrupt, the processor unit 1102 may pause its processing and execute an interrupt service routine (ISR), for example, as described herein.

The storage device 1116 includes a machine-readable medium 1122 on which is stored one or more sets of data structures and instructions 1124 (e.g., software) embodying or utilized by any one or more of the methodologies or functions described herein. The instructions 1124 can also reside, completely or at least partially, within the main memory 1104, static memory 1106, and/or within the processor unit 1102 during execution thereof by the architecture 1100, with the main memory 1104, static memory 1106, and the processor unit 1102 also constituting machine-readable media. Instructions 1124 stored at the machine-readable medium 1122 may include, for example, instructions for implementing the software architecture 1002, instructions for executing any of the features described herein, etc.

While the machine-readable medium 1122 is illustrated in an example to be a single medium, the term "machine-readable medium" can include a single medium or multiple media (e.g., a centralized or distributed database, and/or associated caches and servers) that store the one or more instructions 1124. The term "machine-readable medium" shall also be taken to include any tangible medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including, but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions 1124 can further be transmitted or received over a communications network 1126 using a transmission medium via the network interface device 1120 utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., Wi-Fi, 3G, and 6G LTE/LTE-A or WiMAX networks). The term "transmission medium" shall be taken to include any intangible medium that is capable of storing, encoding, or carrying instructions for execution by the machine, and includes digital or analog communications signals or other intangible medium to facilitate communication of such software.

Various components are described in the present disclosure as being configured in a particular way. A component may be configured in any suitable manner. For example, a component that is or that includes a computing device may be configured with suitable software instructions that program the computing device. A component may also be configured by virtue of its hardware arrangement or in any other suitable manner.

The above description is intended to be illustrative, and not restrictive. For example, the above-described examples (or one or more aspects thereof) can be used in combination with others. Other embodiments can be used, such as by one of ordinary skill in the art upon reviewing the above description. The Abstract is to allow the reader to quickly ascertain the nature of the technical disclosure, for example, to comply with 37 C.F.R. § 1.72(b) in the United States of America. It is submitted with the understanding that it will not be used to interpret or limit the scope or meaning of the claims.

Also, in the above Detailed Description, various features can be grouped together to streamline the disclosure. However, the claims cannot set forth every feature disclosed herein as embodiments can feature a subset of said features. Further, embodiments can include fewer features than those disclosed in a particular example. Thus, the following claims are hereby incorporated into the Detailed Description, with a claim standing on its own as a separate embodiment. The scope of the embodiments disclosed herein is to be determined with reference to the appended claims, along with the full scope of equivalents to which such claims are entitled.

What is claimed is:

1. A system comprising:
   at least one processor; and
   a memory in communication with the at least one processor, wherein the at least one processor is programmed to perform operations comprising:
   accessing first user interest data;
   receiving news data describing a plurality of news items;
   selecting a first news item from the news data based at least in part on the first user interest data;
   receiving user financial data describing at least one financial holding of a first user;
   determining that the first news item is negative for the first user based at least in part on the user financial data;
   receiving, from a first network-enabled device, physiological data describing a physiological condition of the first user at a first time;
   determining to provide the first news item to the first user based at least in part on the physiological data; and
   sending, to a second network-enabled device, alert data instructing the second network-enabled device to modify the operation of the second network-enabled device to generate an alert indicating the first news item.

2. The system of claim 1, wherein the at least one processor is further programmed to perform operations comprising generating the first user interest data based at least in part on the user financial data.

3. The system of claim 1, wherein the at least one processor is further programmed to perform operations comprising:
   receiving, from a network-enabled appliance, appliance usage data describing usage of the network-enabled appliance; and
   generating the first user interest data based at least in part on the appliance usage data.

4. The system of claim 1, wherein the at least one processor is further programmed to perform operations comprising:
   receiving, from a network-enabled appliance, appliance usage data describing usage of the network-enabled appliance; and
   determining a potential financial holding for the first user based at least in part on the appliance usage data, wherein the determining that the first news item is negative for the first user is also based at least in part on the potential financial holding.

5. The system of claim 1, wherein the at east one processor is further programmed to perform operations comprising:
   receiving, from a network-enabled refrigerator, an image depicting a first item in the refrigerator; and
   determining a potential financial holding for the first user based at least in part on the first item.

6. The system of claim 1, wherein the at least one processor is further programmed to perform operations comprising:
   selecting from the plurality of news items an interest set of news items based at least in part on the first user interest data, wherein the interest set of news items comprises the first news item and a second news item; and
   generating a first user news data structure comprising the first news item and the second news item, wherein the first user news data structure comprises a next news item position.

7. The system of claim 6, wherein the at least one processor is further programmed to perform operations comprising:
   determining that the second news item is at the next news item position of the first user news data structure, wherein the second news item is negative for the first user;
   receiving, from the first network-enabled device; second physiological data describing a second physiological condition of the first user at a second time;
   determining not to provide the second news item to the first user based at least in part on the second physiological data; and
   moving the second news item from the next news item position of the first user news data structure.

8. The system of claim 1, wherein the second network-enabled device is a lighting system, and wherein the alert data instructs the lighting system to modify the operation of the lighting system at least by blinking a first light in communication with the lighting system.

9. The system of claim 1, wherein the first network-enabled device is a wearable device, and wherein the physiological data comprises a heart rate of the first user.

10. The system of claim 1, wherein the at least one processor is further programmed to perform operations comprising accessing location data describing a location of the first user, wherein determining to provide the first news item to the first user is also based at least in part on the location data.

11. A method comprising:
    accessing first user interest data;
    receiving news data describing a plurality of news items;
    selecting a first news item from the news data based at least in part on the first user interest data;
    receiving user financial data describing at least one financial holding of a first user;

determining that the first news item is negative for the first user based at least in part on the user financial data;

receiving, from a first network-enabled device, physiological data describing a physiological condition of the first user at a first time;

determining to provide the first news item to the first user based at least in part on the physiological data; and sending, to a second network-enabled device, alert data instructing the second network-enabled device to modify the operation of the second network-enabled device to generate an alert indicating the first news item.

12. The method of claim 11, further comprising generating the first user interest data based at least in part on the user financial data.

13. The method of claim 11, further comprising:

receiving; from a network-enabled appliance, appliance usage data describing usage of the network-enabled appliance; and generating the first user interest data based at least in part on the appliance usage data.

14. The method of claim 11, further comprising:

receiving; from a network-enabled appliance, appliance usage data describing usage of the network-enabled appliance; and determining a potential financial holding for the first user based at least in part on the appliance usage data, wherein the determining that the first news item is negative for the first user is also based at least in part on the potential financial holding.

15. The method of claim 11, further comprising:

receiving from a network-enabled refrigerator an image depicting a first item in the refrigerator; and determining a potential financial holding for the first user based at least in part on the first item.

16. The method of claim 11, further comprising:

selecting from the plurality of news items an interest set of news items based at least in part on the first user interest data, wherein the interest set of news items comprises the first news item and a second news item; and generating a first user news data structure comprising the first news item and the second news item, wherein the first user news data structure comprises a next news item position.

17. The method of claim 16, further comprising:

determining that the second news item is at the next news item position of the first user news data structure; wherein the second news item is negative for the first user;

receiving, from the first network-enabled device, second physiological data describing a second physiological condition of the first user at a second time;

determining not to provide the second news item to the first user based at least in part on the second physiological data; and moving the second news item from the next news item position of the first user news data structure.

18. The method of claim 11, wherein the second network-enabled device is a lighting system, and wherein the alert data instructs the lighting system to modify the operation of the lighting system at least by blinking a first light in communication with the lighting system.

19. The method of claim 11, wherein the first network-enabled device is a wearable device, and wherein the physiological data comprises a heart rate of the first user.

20. The method of claim 11, further comprising accessing location data describing a location of the first user, wherein determining to provide the first news item to the first user is also based at least in part on the location data.

21. A non-transitory machine-readable medium comprising instructions thereon that, when executed by at least one processor, cause the at least one processor to perform operations comprising:

accessing first user interest data;

receiving news data describing a plurality of news items;

selecting a first news item from the news data based at least in part on the first user interest data;

receiving user financial data describing at least one financial holding of a first user;

determining that the first news item is negative for the first user based at least in part on the user financial data;

receiving, from a first network-enabled device, physiological data describing a physiological condition of the first user at a first time;

determining to provide the first news item to the first user based at least in part on the physiological data; and sending, to a second network-enabled device, alert data instructing the second network-enabled device to modify the operation of the second network-enabled device to generate an alert indicating the first news item.

* * * * *

UNITED STATES PATENT AND TRADEMARK OFFICE
CERTIFICATE OF CORRECTION

PATENT NO. : 10,038,975 B1  
APPLICATION NO. : 15/348574  
DATED : July 31, 2018  
INVENTOR(S) : Nelson et al.

Page 1 of 1

It is certified that error appears in the above-identified patent and that said Letters Patent is hereby corrected as shown below:

In the Claims

In Column 18, Line 12, in Claim 5, delete "east" and insert --least-- therefor

In Column 18, Line 39, in Claim 7, delete "device;" and insert --device,-- therefor In Column 19, Line 18, in Claim 13, delete "receiving;" and insert --receiving,-- therefor In Column 19, Line 24, in Claim 14, delete "receiving;" and insert --receiving,-- therefor In Column 20, Line 3, in Claim 17, delete "structure;" and insert --structure,-- therefor Signed and Sealed this  
Twenty-sixth Day of March, 2019

Andrei Iancu  
*Director of the United States Patent and Trademark Office*